United States Patent
Yamanouchi

(10) Patent No.: US 11,426,192 B2
(45) Date of Patent: Aug. 30, 2022

(54) CATHETER FOR REMOVING FOREIGN BODY IN BLOOD VESSEL

(71) Applicants: KAWASUMI LABORATORIES, INC., Saiki (JP); Dai Yamanouchi, Madison, WI (US)

(72) Inventor: Dai Yamanouchi, Madison, WI (US)

(73) Assignees: KAWASUMI LABORATORIES, INC., Saiki (JP); Dai Yamanouchi, Madison, WI (US)

( * ) Notice: Subject to any disclaimer, the term of this patent is extended or adjusted under 35 U.S.C. 154(b) by 478 days.

(21) Appl. No.: 16/130,516

(22) Filed: Sep. 13, 2018

(65) Prior Publication Data
US 2019/0008550 A1    Jan. 10, 2019

Related U.S. Application Data

(63) Continuation of application No. 14/556,827, filed on Dec. 1, 2014, now abandoned.
(Continued)

(51) Int. Cl.
*A61B 17/3207*    (2006.01)
*A61B 17/221*    (2006.01)
*A61B 17/22*    (2006.01)

(52) U.S. Cl.
CPC .... *A61B 17/320758* (2013.01); *A61B 17/221* (2013.01); *A61B 17/32075* (2013.01);
(Continued)

(58) Field of Classification Search
CPC .................. A61B 17/221; A61B 17/11; A61B 17/320758; A61B 17/3207; A61B 17/32;
(Continued)

(56) References Cited

U.S. PATENT DOCUMENTS 4,611,594 A * 9/1986 Grayhack ............ A61B 17/221
606/127
4,811,735 A    3/1989 Nash et al.
(Continued)

FOREIGN PATENT DOCUMENTS

JP         2-61315 U    5/1990
JP    2006-522662 A    10/2006
(Continued)

OTHER PUBLICATIONS

Communication dated May 7, 2019 issued by the Japanese Intellectual Property Office in counterpart Japanese Application No. 2018-109612.
(Continued)

*Primary Examiner* — Dianne Dornbusch
(74) *Attorney, Agent, or Firm* — Sughrue Mion, PLLC

(57) ABSTRACT

A capturing unit provided on a distal end of a second tube can be deformed into a contracted state and an expanded state, in which the capturing unit is deployed to form a capturing chamber. The capturing chamber has an opening area decreased as it goes from a distal end opening of the capturing chamber toward a proximal end opening of the capturing chamber. A third tube rotatable relative to the second tube and a cutting unit provided on a distal end of the third tube for cutting a foreign substance are arranged in a second lumen. In the expanded state of the capturing unit, the cutting unit is arranged more toward the proximal end opening of the capturing chamber than the distal end opening.

8 Claims, 8 Drawing Sheets

Related U.S. Application Data

(60) Provisional application No. 61/911,022, filed on Dec. 3, 2013.

(52) U.S. Cl.
CPC ............... *A61B 17/320725* (2013.01); *A61B 2017/22001* (2013.01); *A61B 2017/2212* (2013.01); *A61B 2017/2215* (2013.01); *A61B 2017/320716* (2013.01); *A61B 2017/320766* (2013.01); *A61B 2017/320775* (2013.01)

(58) Field of Classification Search
CPC ...... A61B 17/320016; A61B 17/32002; A61B 17/22031; A61B 17/22032; A61B 17/2215; A61B 17/320716; A61B 17/2212; A61B 17/22079; A61B 17/320028; A61B 17/320032; A61B 17/22034; A61B 17/22035; A61B 17/22084
See application file for complete search history.

(56) References Cited

U.S. PATENT DOCUMENTS

| | | | | |
|---|---|---|---|---|
| 4,927,426 A * | 5/1990 | Dretler | ............... | A61B 18/245 606/2.5 |
| 5,011,488 A * | 4/1991 | Ginsburg | ......... | A61M 25/0074 606/159 |
| 5,092,839 A * | 3/1992 | Kipperman | ......... | A61M 25/104 128/898 |
| 5,102,415 A * | 4/1992 | Guenther | ............... | A61B 17/22 604/103.05 |
| 5,190,561 A * | 3/1993 | Graber | ............. | A61B 17/00234 606/114 |
| 5,263,959 A * | 11/1993 | Fischell | ............. | A61B 17/3207 606/167 |
| 5,318,576 A | 6/1994 | Plassche et al. | | |
| 5,320,627 A | 6/1994 | Sorensen et al. | | |
| 5,836,868 A | 11/1998 | Ressemann et al. | | |
| 5,891,153 A | 4/1999 | Peterson et al. | | |
| 5,897,567 A | 4/1999 | Ressemann et al. | | |
| 5,971,938 A | 10/1999 | Hart et al. | | |
| 6,800,083 B2 * | 10/2004 | Hiblar | ............ | A61B 17/320758 606/171 |
| 6,808,531 B2 | 10/2004 | Lafontaine et al. | | |
| 6,958,069 B2 * | 10/2005 | Shipp | ............... | A61B 17/00234 606/127 |
| 7,153,320 B2 * | 12/2006 | Euteneuer | ............... | A61F 2/011 606/200 |
| 7,837,702 B2 * | 11/2010 | Bates | ..................... | A61F 2/014 606/200 |
| 8,088,140 B2 | 1/2012 | Ferrera | | |
| 9,149,609 B2 * | 10/2015 | Ansel | .................. | A61B 17/221 |
| 9,254,371 B2 * | 2/2016 | Martin | ................. | A61M 25/10 |
| 10,039,900 B2 * | 8/2018 | di Palma | ............. | A61B 17/221 |
| 2002/0019640 A1 | 2/2002 | McGuckin, Jr. | | |
| 2002/0151917 A1 * | 10/2002 | Barry | ............ | A61B 17/320758 606/159 |
| 2003/0014074 A1 | 1/2003 | Cherfas et al. | | |
| 2004/0204738 A1 | 10/2004 | Weber et al. | | |
| 2005/0059981 A1 | 3/2005 | Poll | | |
| 2006/0229645 A1 | 10/2006 | Bonnette et al. | | |
| 2008/0033467 A1 * | 2/2008 | Miyamoto | ..... | A61B 17/320725 606/180 |
| 2009/0292307 A1 | 11/2009 | Razack et al. | | |
| 2009/0299393 A1 * | 12/2009 | Martin | ................. | A61B 17/221 606/159 |
| 2011/0257674 A1 | 10/2011 | Evert | | |
| 2011/0301634 A1 | 12/2011 | Aklog et al. | | |
| 2012/0016407 A1 | 1/2012 | Sakai | | |
| 2012/0035635 A1 | 2/2012 | Weber et al. | | |
| 2012/0059309 A1 * | 3/2012 | di Palma | ............. | A61M 25/007 604/22 |
| 2012/0059356 A1 * | 3/2012 | di Palma | ............. | A61B 17/221 604/509 |
| 2012/0197277 A1 | 8/2012 | Stinis | | |
| 2012/0239064 A1 | 9/2012 | Cartier et al. | | |
| 2013/0030461 A1 * | 1/2013 | Marks | ..................... | A61F 2/013 606/200 |
| 2014/0005717 A1 | 1/2014 | Martin et al. | | |
| 2014/0052103 A1 | 2/2014 | Cully | | |
| 2014/0257352 A1 | 9/2014 | Weber et al. | | |
| 2016/0066936 A1 | 3/2016 | Weber et al. | | |
| 2017/0325830 A1 | 11/2017 | Martin et al. | | |

FOREIGN PATENT DOCUMENTS

| | | |
|---|---|---|
| JP | 2009-66178 A | 4/2009 |
| JP | 2010-188068 A | 9/2010 |
| JP | 2013-233454 A | 11/2013 |
| WO | 2010148273 A1 | 12/2010 |

OTHER PUBLICATIONS

Communication dated Nov. 12, 2019, issued by the Japanese Patent Office in counterpart Japanese Application No. 2018-109612.
Office Action dated Dec. 5, 2017, by the Japanese Patent Office in counterpart Japanese Application No. 2014-018855.
Search Report dated Mar. 19, 2015, issued by the European Patent Office in counterpart European Application No. 14195415.6.

\* cited by examiner

FIG.7A
FIG.7B
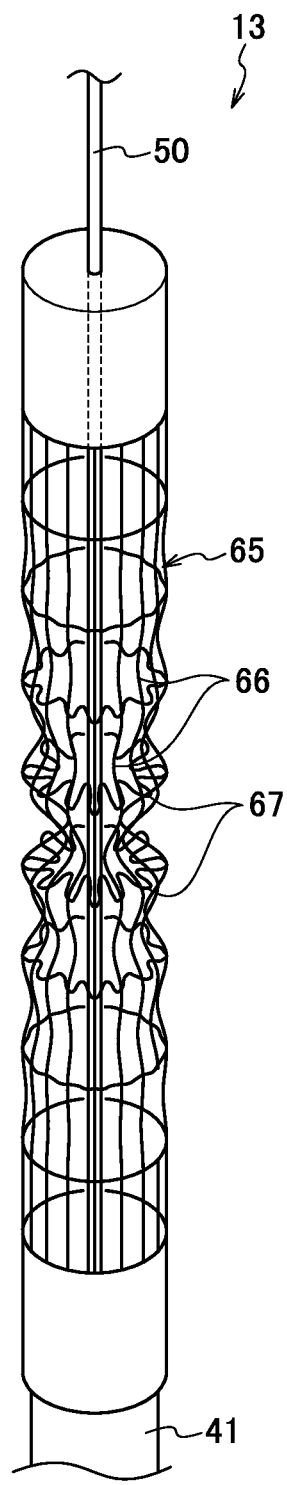
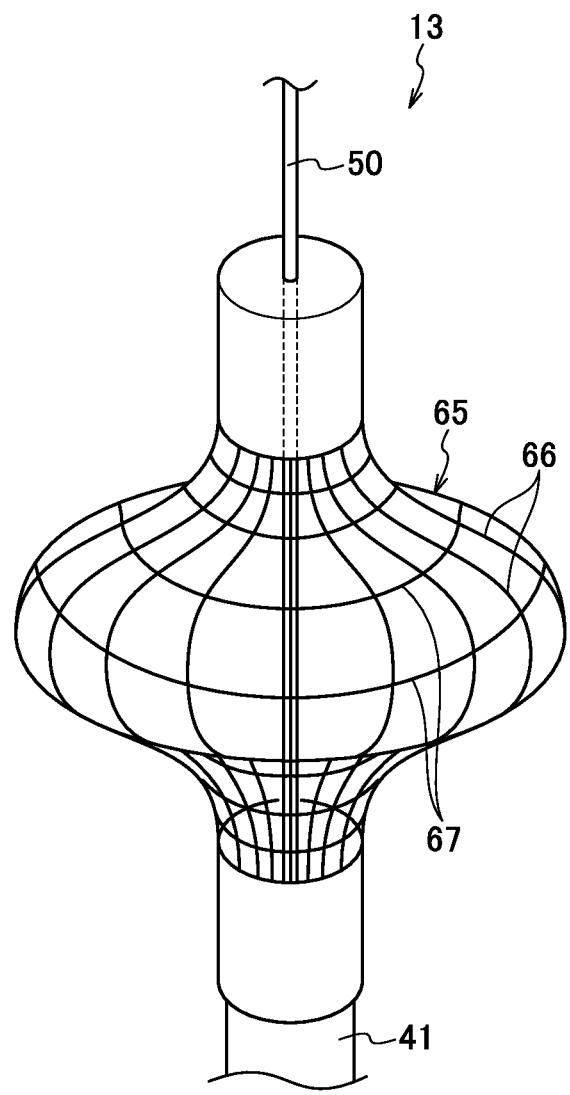

CATHETER FOR REMOVING FOREIGN BODY IN BLOOD VESSEL

CROSS-REFERENCE TO RELATED APPLICATION

This application is a continuation of U.S. patent application Ser. No. 14/556,827, filed Dec. 1, 2014 which claims the benefit of priority from U.S. Provisional Patent Application No. 61/911,022 filed on Dec. 3, 2013; the entire contents of which are incorporated herein by reference.

TECHNICAL FIELD

The present invention relates to a catheter for removing foreign body in blood vessel, and more particularly, to a catheter for removing foreign body in blood vessel, which captures/crushes a foreign substance, such as thrombus, which embolizes a blood vessel and is adhered on a blood vessel wall, and thus allows the foreign substance to be effectively sucked and removed through the catheter to the outside of the body.

BACKGROUND ART

To reperfuse a blood vessel, in which stenosis or occlusion is caused due to atheromatous plaque or thrombus, an occlusion substance within the blood vessel has to be removed. A balloon catheter in which a foreign substance removing filter, such a annular wire or a mesh is stored in a catheter tube, or various apparatuses, in which a metal wire is expanded in a coil shape or in three dimensional directions so that thrombus is caught or scrapped by the metal wire, thereby removing the thrombus, have been previously proposed. Even in the case of the catheter having such a foreign substance removing filter, it is difficult to capture all fragments of atheromatous plaque or thrombus peeled from a blood vessel wall, and in addition, there are problems in that in a case of a large thrombus or the like, the thrombus is clogged in the catheter or does not enter the catheter, or the like. If such thrombus, which cannot be recovered and is freed, enters a peripheral vascular, there is a risk of causing peripheral vascular occlusion or the like. Therefore, development of an apparatus in which thrombus removed by a balloon or the like can be reliably and effectively recovered, is strongly required.

Previously, as a suction catheter, which sucks and removes thrombus present in a blood vessel for treating stenosis due to the thrombus, a suction catheter has been known, which has an outer tube and an inner tube and in which a suction device is connected to a proximal end of the inner tube and an elastic deformable portion formed to be deformable into a contracted state and an expanded state is arranged on a distal end thereof, so that the suction device sucks and removes a foreign substance, such as thrombus, from the elastic deformable portion in the expanded state where a suction port thereof is expanded in a tapered shape (e.g., see Patent Document 1). Also, an apparatus has been known, in which, on an distal end of a catheter having a suction device, a propeller rotatably supported in the catheter is arranged, and when thrombus is sucked into a tip portion of the catheter by the suction device, the thrombus is crushed by the propeller and then is sucked and removed (e.g., see Patent Document 2).

CITATION LIST

Patent Document

Patent Document 1: JP 2009-66178 A
Patent Document 2: JP 2-61315 U

SUMMARY OF INVENTION

Technical Problem

However, in the suction catheter disclosed in Patent Document 1, there has been a problem in that a larger thrombus than an opening of the inner tube cannot be satisfactorily sucked and removed. Also, in the catheter of Patent Document 2, although the sucked thrombus is crushed by the propeller, a large thrombus, which cannot be sucked through an opening of the catheter, cannot be cut by the propeller, because a location of an end of the propeller coincides with a location of the distal end of the catheter as viewed along a tube axis of the catheter. Even if a portion of the thrombus has been sucked in the tip portion of the catheter, the cutting process has to be sequentially performed from the sucked portion, as a result of which there is a possibility that much time is taken to cut the entire thrombus.

The present invention has been made keeping in mind the above problems, and an object of the invention is to provide a catheter for removing foreign body in blood vessel, in which a foreign substance in vivo, such as thrombus, can be nodulized to be effectively sucked and removed.

Technical Solution

The above object of the present invention is achieved by the following configurations:

(1) A catheter for removing foreign body in blood vessel, including:
   a tube that has a lumen; and
   a capturing unit that is provided on a distal end of the tube and that can have a contracted state, in which the capturing unit is contracted, and an expanded state, in which the capturing unit is expanded to form a capturing chamber;
   wherein the catheter is characterized by further including:
   a power transmitting member that is arranged in the lumen and that can rotate relative to the tube; and
   a cutting unit that is provided on a distal end of the power transmitting member for cutting a foreign substance flowed into the capturing unit;
   wherein the capturing chamber has an opening area decreased gradually from a distal end opening of the capturing chamber toward a proximal end opening of the capturing chamber; and
   in the expanded state of the capturing unit, the cutting unit is arranged more toward the proximal end opening of the capturing chamber than the distal end opening of the capturing chamber.

(2) The catheter for removing foreign body in blood vessel according to (1), characterized in that:
   the power transmitting member is another tube having a lumen; and
   a guide wire can be inserted through the lumen of said another tube.

(3) The catheter for removing foreign body in blood vessel according to (1) or (2), characterized in that:
the power transmitting member is another tube having a lumen; and
a guide unit which guides a foreign substance into the capturing chamber can be inserted through the lumen of said another tube.
(4) The catheter for removing foreign body in blood vessel according to (3), characterized in that:
a radiographic marker is provided to check a distance between the guide unit and the cutting unit visually.
(5) The catheter for removing foreign body in blood vessel according to any one of (1) to (4), characterized in that:
the cutting unit is a foldable propeller-shaped member.
(6) The catheter for removing foreign body in blood vessel according to (5), characterized in that:
unevenness is formed on an inner surface of the capturing chamber along a circumferential direction thereof.
(7) The catheter for removing foreign body in blood vessel according to any one of (1) to (4), characterized in that:
the cutting unit is an expandable meshed member.
(8) The catheter for removing foreign body in blood vessel according to any one of (1) to (7), characterized in that:
the power transmitting member is movable relative to the tube only toward a distal end thereof.

Advantageous Effects

According to the catheter for removing foreign body in blood vessel of the present invention as described in (1), because the capturing chamber has an opening area decreased as it goes from a distal end opening of the capturing chamber toward a proximal end opening of the capturing chamber and also, in the expanded state of the capturing unit, the cutting unit is arranged more toward the proximal end opening of the capturing chamber than the distal end opening of the capturing chamber, a foreign substance, such as thrombus, can be guided from the distal end opening having a large opening area in the capturing chamber toward the proximal end opening having a small opening area, and thus can be effectively condensed in the proximal end opening. Also, by cutting the foreign substance, which has been condensed in the proximal end opening of the capturing chamber, by the cutting unit, the foreign substance can be effectively nodulized. Therefore, a large foreign substance, which would not be previously sucked into a catheter, can be also nodulized to be effectively sucked and removed. In addition, because the cutting unit is arranged more toward the proximal end opening of the capturing chamber than the distal end opening of the capturing chamber, the cutting unit is not exposed in a blood vessel upon cutting, thereby ensuring safety.

According to the catheter for removing foreign body in blood vessel of the present invention as described in (2), because the power transmitting member is another tube having a lumen, through which a guide wire can be inserted, the catheter can be directed by the guide wire to be reliably guided to a site, where the foreign substance is generated.

According to the catheter for removing foreign body in blood vessel of the present invention as described in (3), because the power transmitting member is another tube having a lumen, through which a guide unit for guiding a foreign substance into the capturing chamber can be inserted, the foreign substance can be effectively guided and condensed into the capturing chamber by the guide unit.

According to the catheter for removing foreign body in blood vessel of the present invention as described in (4), because a radiographic marker is provided to allow a distance between the guide unit and the cutting unit to be seen by eyes, contact between the cutting unit and a balloon can be prevented, thereby avoiding damage of the guide unit by the cutting unit.

According to the catheter for removing foreign body in blood vessel of the present invention as described in (5), because the cutting unit is a foldable propeller-shaped member, even a large foreign substance can be sucked and removed by reliably cutting and nodulizing the foreign substance by the propeller-shaped member.

According to the catheter for removing foreign body in blood vessel of the present invention as described in (6), because unevenness is formed on an inner surface of the capturing chamber along a circumferential direction thereof, the foreign substance can be ground and crushed by the unevenness formed on the inner surface of the capturing chamber and the propeller-shaped member, thereby effectively nodulizing the foreign substance.

According to the catheter for removing foreign body in blood vessel of the present invention as described in (7), because the cutting unit is an expandable meshed member, even a large foreign substance can be sucked and removed by reliably cutting and nodulizing the foreign substance by the meshed member.

According to the catheter for removing foreign body in blood vessel of the present invention as described in (8), because the power transmitting member is movable relative to the tube only toward a distal end thereof, the power transmitting member is moved relative to the tube toward the distal end side thereof after cutting the foreign substance, so that the nodulized foreign substance can be effectively sucked from the proximal end opening of the capturing chamber. Also, during insertion into the blood vessel, movement of the power transmitting member relative to the tube toward the proximal end side thereof is restricted, so that when inserting the tube, a location of the power transmitting member is restricted, thereby allowing an easy insertion of the tube.

BRIEF DESCRIPTION OF DRAWINGS

FIG. 5A is in a contracted state, according to a second embodiment, and FIG. 5B is a perspective view of the cutting unit, which is in an expanded state.

FIGS. 7A and 7B are perspective views of a cutting unit. FIG. 7A is in a contracted state, according to a third embodiment, and FIG. 7B is a perspective view of the cutting unit, which is in an expanded state.

DESCRIPTION OF EMBODIMENTS

Each of embodiments of a catheter for removing foreign body in blood vessel according to the present invention will be now described in detail on the basis of the drawings.

First Embodiment

Figure 1:
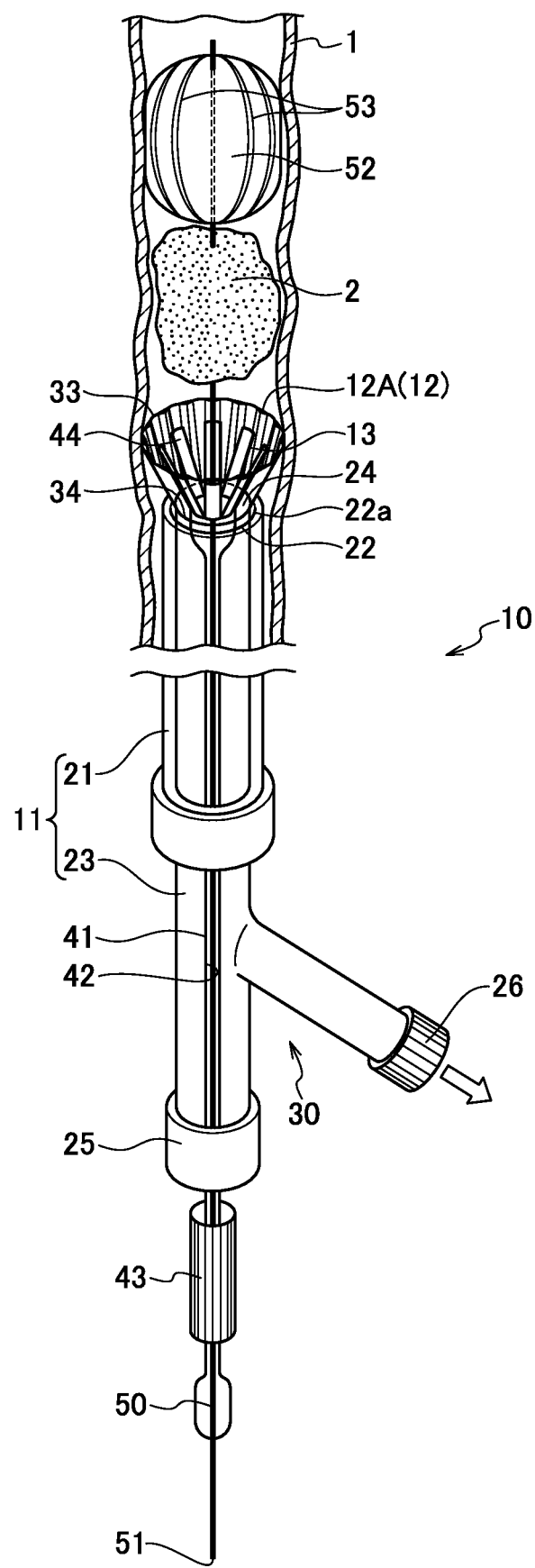
FIG. 1 is an explanatory view showing a configuration of a first embodiment of a catheter for removing foreign body in blood vessel according to the present invention.

FIG. 1 is a configuration view of a catheter for removing foreign body in blood vessel according to a first embodiment of the present invention. As shown in FIG. 1, the catheter for removing foreign body in blood vessel 10 has a sheath 11, a capturing unit 12 and a cutting unit 13.

The sheath 11 includes a first tube 21 having a first lumen 22 and a second tube 23 having a second lumen 24 and has a double lumen structure in which the second tube 23 is inserted through the first lumen 22 of the first tube 21 and thus is adapted to be movable in first lumen 22 in an axial direction of the first tube 21.

The first and second tubes 21 and 23 are molded of an elastically deformable material, such as polyethylene, polyethylene terephthalate, polypropylene, polyurethane, polyamide elastomer, polyimide, polyimide elastomer, copolymers thereof, silicone rubber, or natural rubber, and have a substantially uniform outer diameter over a longitudinal direction thereof. Also, the first and second lumens 22 and 24 are likewise formed to have a substantially uniform inner diameter over a longitudinal direction thereof.

An operation unit 30 is provided on a proximal end side of the second tube 23. The operation unit 30 is provided with a first port 25 and a second port 26. The first port 25 is communicated with the second lumen 24 and provided on an axis of the sheath 11 (second tube 23), and also has an opening fluid-tightly occluded by a valve body, not shown, formed of silicone rubber or the like. A third tube 41 as described below is inserted in the first port 25 to extend through the valve body and then to be inserted through the second lumen 24.

The second port 26 is communicated with the second lumen 24 and formed to extend from the second tube 23 in a direction intersecting the axis of the sheath 11. Other devices (not shown), such as a syringe, is connected to the second port 26 to impart a suction force to the second lumen 24, so that a foreign substance 2, such as thrombus formed within a blood vessel 1, are sucked and removed through the second port 26 to the outside of a body.

Figure 2:
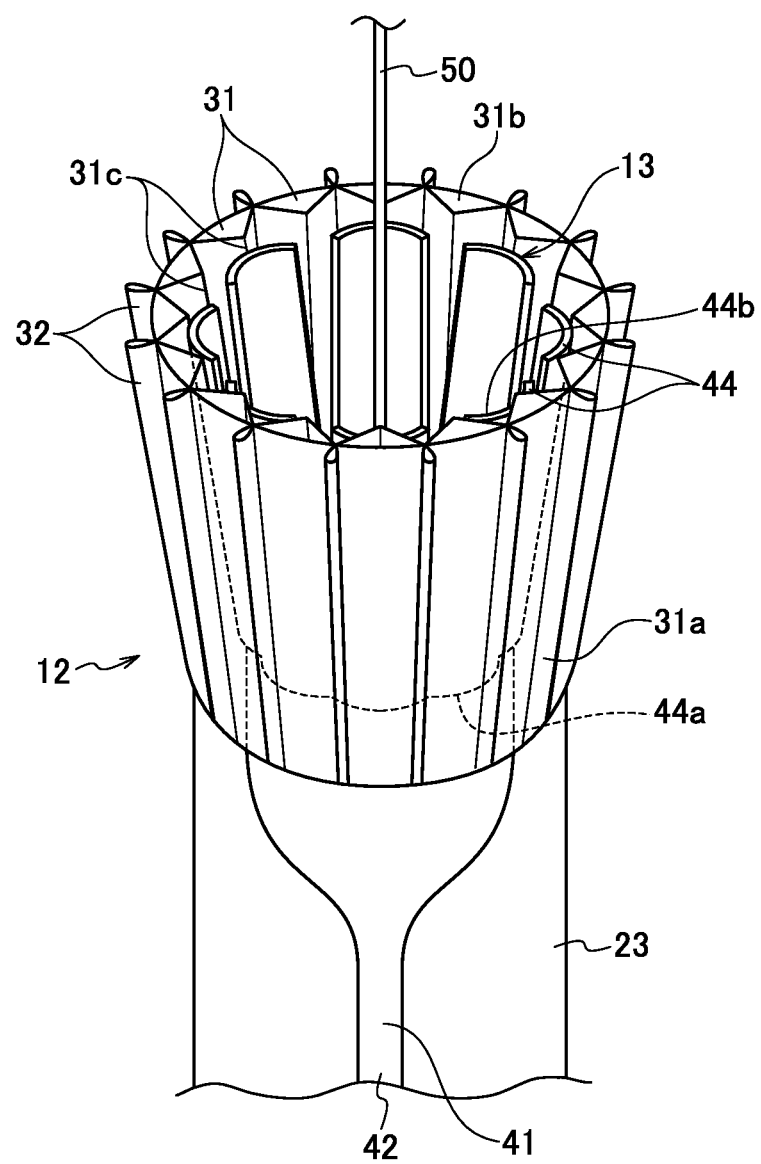
FIG. 2 is an enlarged perspective view of a capturing unit, which is in a contracted state, and a cutting unit, which is received in the capturing unit in a contracted state, of the catheter for removing foreign body in blood vessel shown in FIG. 1.
Figure 3:
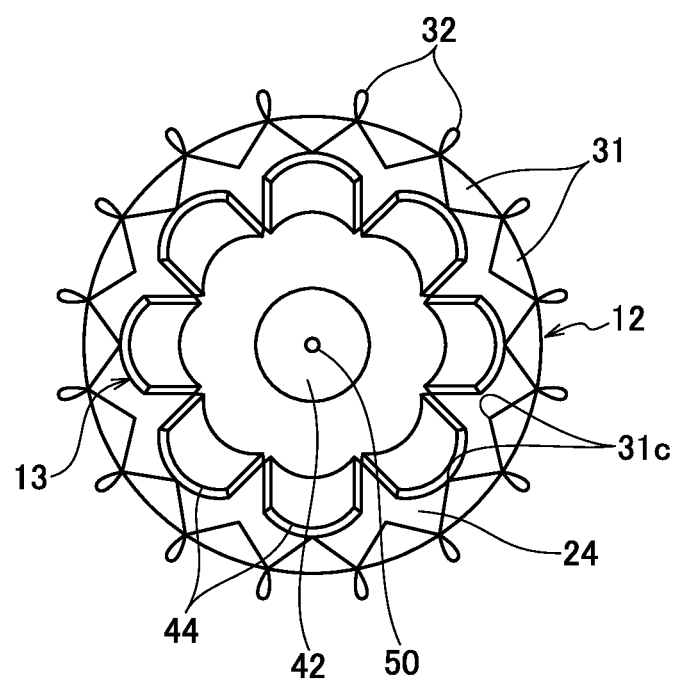
FIG. 3 is a top view of FIG. 2.
Figure 4:
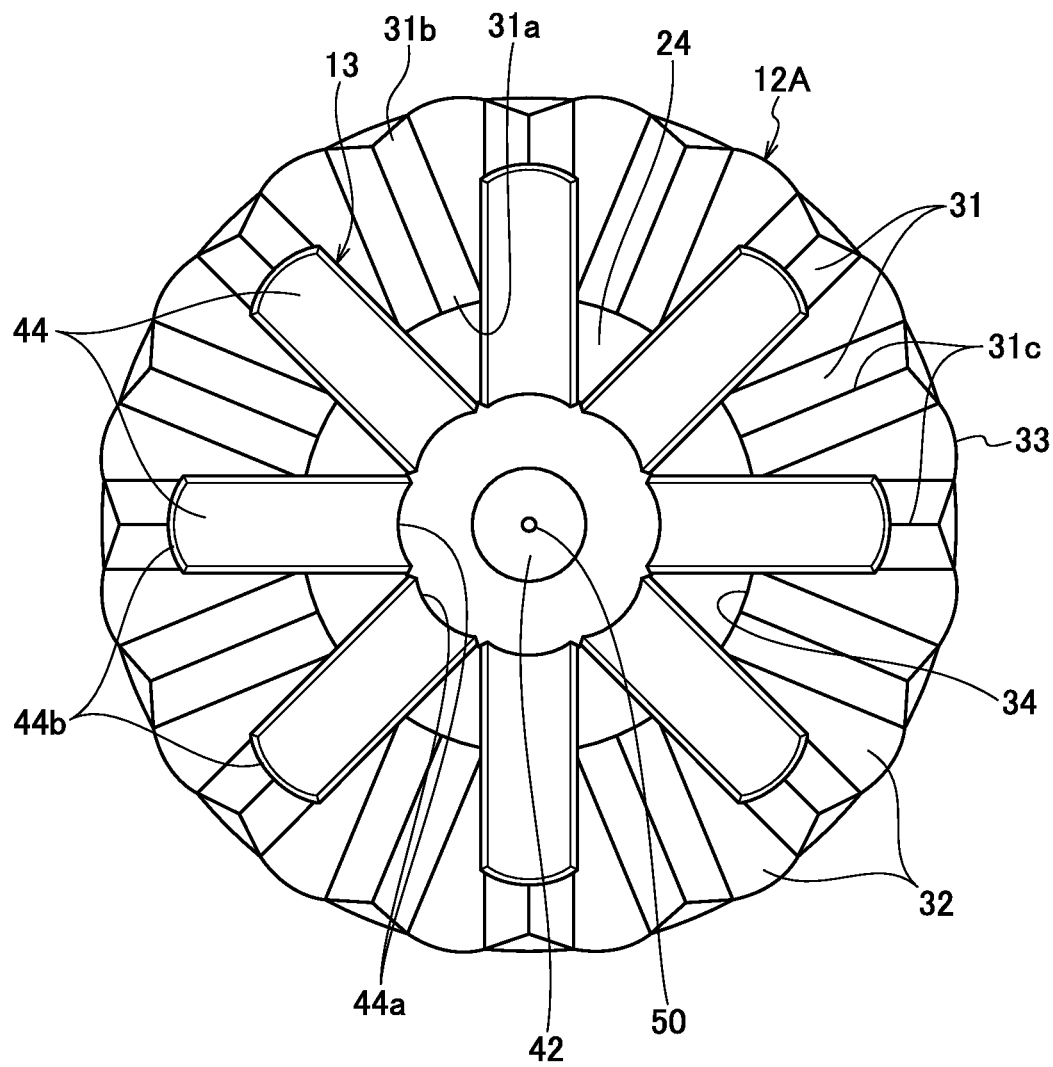
FIG. 4 is an enlarged top view of the capturing unit and the cutting unit, which are in an expanded state.

Referring to FIGS. 2 and 4, the capturing unit 12 is provided on a distal end of the second tube 23 and adapted to be deformable into a contracted state (see FIGS. 2 and 3), in which the capturing unit is received in the first lumen 22, and an expanded state (see FIGS. 1 and 4), in which the capturing unit is deployed in a generally umbrella shape by a self-restoring force to form a capturing chamber 12A.

The capturing unit 12 has a plurality of generally triangle column-shaped frame portions 31 (16 pieces in the embodiment shown in the drawings) made of a shape memory alloy (for example, Ni—Ti alloy), in which the expanded state is shape-memorized, and a plurality of sheet portions 32 (16 pieces in the embodiment shown in the drawings) formed in a membrane shape for connecting the adjacent frame portions 31 to each other and being deployable in an umbrella shape in accordance with expansion of the frame portions 31.

The frame portions 31 are arranged at substantially equal intervals in a circumferential direction and extend in an axial direction in a state where proximal end sides 31a of the frame portions 31 are fixed on an outer periphery of a tip of the second tube 23 and distal end sides 31b of the frame portions 31 are opened. In the contracted state, in which frame portions are received in the first lumen 22, each frame portion 31 is pushed and contracted against the restoring force, by which the shape memory alloy is to be expanded, because an outer peripheral surface of each frame portion 31 is abutted to and constrained by an inner peripheral surface (first lumen 22) of the first tube 21. Namely, the capturing unit 12 in the contracted state forms a generally cylinder because the distal end sides 31b of the plurality of frame portions 31 are aligned on a circumference. The frame portions 31 in the contracted state are arranged so that one ridge 31c of three ridges, which extend along an axial direction of the second tube 23, protrudes toward an inner surface of the cylinder. Therefore, on an inner surface of the capturing unit 12, unevenness along a circumferential direction thereof is formed. Also, the frame portions 31 in a natural state, in which constraint by the first lumen 22 is released, are deployed by the self-restoring force to become the expanded state.

The sheet portions 32, which have a foldable flexibility, extend in the axial direction of the second tube 23 and also are fixed on lateral surfaces of the adjacent frame portions 31. In addition, proximal end sides of the sheet portions 32 are fixed on the outer periphery of the tip of the second tube 23. The folded sheet portions 32 are deployed in an umbrella shape when the frame portions 31 become the expanded state, and thus cover between the adjacent frame portions 31 in a membrane shape.

Thus, in the contracted state (see FIGS. 2 and 3), in which the capturing unit is received in the first lumen 22, the capturing unit 12 is adapted so that the distal end sides 31b of the plurality of frame portions 31 are gathered in a circumference shape against the restoring force of the shape memory alloy and the sheet portions 32 are folded, thereby becoming a generally cylindrical shape. Then, when the capturing unit 12, which has been received in the first lumen 22 in the contracted state, is pushed out from an opening 22a on a distal end of the first lumen 22, constraint thereof by the first lumen 22 is released and thus the plurality of frame portions 31 are deployed in a generally umbrella shape by spacing the distal end sides 31b from each other by the self-restoring force, thereby forming the capturing chamber 12A (see FIG. 4).

Meanwhile, it is not necessary for the frame portions 31 to be made of a shape memory alloy, in which the expanded state is shape-memorized, and accordingly, the sheet portions 32 may be formed by a balloon. In this case, in a state, where a fluid has not been introduced into the balloon, the balloon is folded and also the frame portions 31 are also contracted so that the capturing unit 12 exhibits the contracted state, whereas in a state, where the fluid has been introduced into the balloon, the balloon is inflated and thus the frame portions 31 are also deployed in accordance with expansion of the balloon, as a result which the capturing unit 12 forms the capturing chamber 12A.

As shown in FIG. 1, the capturing chamber 12A is adapted to have an opening area gradually decreased as it goes from a distal end opening 33 of the capturing chamber 12A toward a proximal end opening 34 of the capturing chamber 12A. Meanwhile, a shape of the capturing chamber 12 shown in the drawings is formed in a tapered shape, in which the frame portions 31 have a linear shape, but the present invention is not limited thereto, and accordingly, a middle part in axial direction of the frame portions 31 may be formed in a shape, which is convex or concave toward an inner wall of the blood vessel 1, and in this case, the shape of the capturing chamber 12A becomes a bowl shape or a trumpet shape.

The cutting unit 13 is intended to nodulize the foreign substance 2, which has been flowed into the capturing chamber 12A, by cutting, crushing or grinding, and is provided on a distal end of the third tube 41 as shown in FIGS. 1 to 4 and arranged in the capturing chamber 12A more toward the proximal end opening 34 than the distal end opening 33. As used herein, the term 'to nodulize' means cutting, crushing or grinding the foreign substance 2, such as thrombus, to have a size suitable to be sucked and removed through the second lumen 24 without causing clogging.

The third tube 41, which has a third lumen 42, is inserted into the second lumen 24 through the valve body (not shown) of the first port 25 and rotatable relative to the second tube 23, and also is arranged to be axially movable by a predetermined distance only toward a distal end side thereof. The third tube 41 is provided on a proximal end side thereof with a spinning rod 43 for operating the cutting unit 13 (see FIG. 1), and by rotating or axially pushing and pulling the spinning rod 43, the cutting unit 13 is rotated or translated relative to the second tube 23. Namely, the third tube 41 serves as a power transmitting member for rotating and moving the cutting unit 13.

The cutting unit 13 according to the present embodiment has a plurality of blades 44 (8 pieces in the embodiment shown in the drawings), which have one ends 44a on proximal end sides thereof fixed on a distal end of the third tube 41 and the other ends 44b on distal end sides thereof being opened, and are arranged at substantially equal intervals in a circumferential direction to take a propeller shape, and also extend in an axial direction.

Each blade 44 has an arc-shaped cross-section shape, which is swelled outward, i.e., toward an inner peripheral surface of the capturing chamber 12A, and is formed of a shape memory alloy (for example, Ni—Ti alloy), in which an expanded state thereof is shape-memorized. The blades 44 in a natural state are urged by a restoring force of the shape memory alloy, so that the other ends 44b on the distal end sides of the blades 44 are flared in a direction spaced away from each other, i.e., each blade 44 is radially flared. Further, when being received in the capturing unit 12, an outer peripheral surface of each blade 44 is abutted to and constrained by the frame portions 31, and thus becomes a contracted state (see FIGS. 2 and 3), in which the other ends 44b on the distal end sides thereof are aligned on a circumference against the restoring force of the shape memory alloy.

Namely, the blades 44 become a contracted state when having been received in the contracted capturing unit 12, and the plurality of blades 44 are aligned in a cylinder shape (see FIG. 2). In addition, if the capturing unit 12 is expanded to form the capturing chamber 12A, the blades 44 are also released from constraint thereof by the frame portions 31 and are flared by the restoring force of the shape memory alloy to become a deployed state (see FIG. 4).

As shown in FIG. 1, a guide wire 50, which is provided on a tip end thereof with a balloon 52 as a guide unit, is inserted through the third lumen 42 of the third tube 41. The balloon 52 serves to guide the foreign substance 2 to the capturing chamber 12A and can be expanded/contracted by a liquid (such as a contrast medium) supplied from a lumen 51 of the guide wire 50. Meanwhile, it is not necessary to provide the balloon 52 on the guide wire 50, and accordingly, a balloon catheter other than the guide wire 50 may be employed.

The balloon 52 is formed of a general material, such as polyamide elastomer. The balloon 52 has an outer surface covered with a wire material 53, which is a protection member for protecting the balloon 52 from the blades 44 and the like. Preferably, the wire material 53 is formed of Ni—Ti alloy or the like having an X-ray contrast property to allow a location thereof in vivo to be checked from the outside of a body under X-ray illumination, and serves as a radiographic marker. However, the wire material 53 is not necessary to be made of a metal, and accordingly may be made of a resin.

In addition, the blades 44 are likewise preferably formed of alloy, such as Ni—Ti alloy, having an X-ray contrast property to serve as a radiographic marker. Therefore, locations of the balloon 52 and the blades 44 can be checked from the outside of the body, and thus when the foreign substance 2, such as thrombus is nodulized by the blades 44 while being condensed in the capturing chamber 12A by the balloon 52 as described below, interference between the balloon 52 and the blades 44 can be prevented.

Meanwhile, the radiographic markers are not limited to the balloon 52 or the blades 44, and accordingly, rings (not shown) or the like formed of a material having an X-ray contrast property may be arranged at suitable locations.

Alternatively, Ni—Ti alloy may be substituted with a superelastic alloy, such as Au—Cd alloy, Cu—Al—Ni alloy, Ni—Ti—Co alloy, or Ni—Ti—Cu alloy, which all have an X-ray contrast property.

In addition, the guide unit provided on the tip end of the guide wire 50 is not limited to the balloon 52, and for example, a thrombus capturing instrument made of a wire material formed in a coil shape (see JP 2010-188068 A) or the like may be employed.

Next, a method of using the catheter for removing foreign body in blood vessel 10 will be described.

First, as shown in FIG. 1, the guide wire 50 is inserted through the blood vessel 1 and the contracted balloon 52 provided on the tip of the guide wire 50 is inserted to a location, where is located beyond a site to be treated, in which the foreign substance 2, such as thrombus, exists, Subsequently, in a state where the contracted capturing unit 12 is received in the first lumen 22, and also the contracted cutting unit 13 is received in the capturing unit 12, the first, second and third tubes 21, 23 and 41 are inserted in the blood vessel 1 along the guide wire 50, and then, distal ends of the first, second and third tubes 21, 23 and 41, i.e., the capturing unit 12 and the cutting unit 13, which all are received in the first lumen 22 to be in the contracted state, are positioned in front of the foreign substance 2.

When the capturing unit 12 and the cutting unit 13 are pushed out from the distal end of the first tube 21 by operating the operation unit 30 of the second tube 23 and the spinning rod 43 of the third tube 41, as shown FIGS. 1 and 4, the capturing unit 12 are deployed in a generally umbrella shape by the restoring force of the frame portions 31 made of the shape memory alloy to form the capturing chamber 12A, and also the blades 44 made of the shape memory alloy are flared by the restoring force thereof so that the cutting unit 13 becomes a deployed state.

Then, after a fluid is supplied from the lumen 51 of the guide wire 50 to inflate the balloon 52, the guide wire 50 is retracted so that the foreign substance 2, such as thrombus, is guided into the capturing chamber 12A by the balloon 52. Because the capturing chamber 12A has an opening area gradually decreased as it goes from the distal end opening 33 of the capturing chamber 12A toward the proximal end opening 34 of the capturing chamber 12A, the foreign substance 2 is effectively condensed in the proximal end opening 34 side of the capturing chamber 12A, i.e., in the vicinity of the blades 44.

At this time, when the spinning rod 43 is rotated, the foreign substance 2 is cut by the rotating blades 44 and also ground between the frame portions 31 of the capturing chamber 12A and the blades 44 to be nodulized. Because unevenness is formed on the inner surface of the capturing chamber 12A by the ridges 31c of the triangle column-shaped frame portions 31, a resistance is applied to the foreign substance 2 by the unevenness so that the foreign substance 2 can be reliably nodulized without rotating together with the blades 44. Meanwhile, the spinning rod 43 may be manually rotated, but may be rotated by a power, such as a motor.

After the foreign substance 2 has been nodulized by the blades 44, other devices, such as a syringe, connected to the second port 26, are activated to build a negative pressure inside the second lumen 24, so that the nodulized foreign substance 2 is sucked and removed from the second port 26 to the outside of the body. At this time, by operating the spinning rod 43 to move the blades 44 in a direction toward a distal end thereof and thus to widen a gap between a distal end-side opening of the second lumen 24 and the blades 44, a relatively large foreign substance 2 can be also effectively sucked and removed.

In addition, as an alternative method, the blades 44 may be moved to a base of the second tube 23 (the vicinity of the first port 25) and then the foreign substance may be sucked and removed from the second port 26. In this case, the third tube 41 has to be provided to be axially movable toward a proximal end side of the second tube 23 as well.

After suction and removal of the foreign substance 2 is ended, the capturing unit 12 (capturing chamber 12A) and the cutting unit 13, which are in the expanded state, are retracted into the first lumen 22 of the first tube 21 to become the contracted state against the restoring force of each thereof, and then the first, second and third tubes 21, 23 and 41 are withdrawn from the blood vessel 1 and also after flatting the balloon 52, the guide wire 50 together with the balloon 52 is withdrawn from the blood vessel 1.

Meanwhile, although the foreign substance 2, such as thrombus, is guided into the capturing chamber 12A by the balloon 52 in the foregoing description, the balloon 52 is not used, but the foreign substance 2 may be guided into the capturing chamber 12A by only suction from the second port 26. In this case, the balloon 52 is not required and also the guide wire 50 can be omitted.

As described above, according to the catheter for removing foreign body in blood vessel 10 of the present embodiment, the capturing unit 12 is provided on the distal end of the second tube 23 and the capturing unit 12 can be deformed into a contracted state and an expanded state in which the capturing chamber 12A having an opening area decreased as it goes from the distal end opening 33 toward the proximal end opening 34, is formed. Because the third tube 41, which is rotatable relative to the second tube 23, and the cutting unit 13, which is provided on the distal end of the third tube 41 and arranged on the proximal end opening 34 side of the capturing chamber 12A to cut the foreign substance 2 captured in the capturing chamber 12A, are disposed in the second lumen 24, the foreign substance 2, such as thrombus, can be guided from the distal end opening 33 having a large opening area toward the proximal end opening 34 having a small opening area, and thus can be effectively condensed in the proximal end opening 34. Also, by cutting or grinding the foreign substance 2, which has been condensed in the proximal end opening 34 of the capturing chamber 12A, by the cutting unit 13, the foreign substance 2 can be effectively nodulized. Therefore, a large foreign substance 2, which would not be previously sucked into a catheter, can be also effectively sucked and removed. In addition, because the cutting unit 13 is arranged more toward the proximal end opening 34 of the capturing chamber 12A than the distal end opening 33 of the capturing chamber 12A, the cutting unit 13 is not exposed in the blood vessel 1 upon cutting, thereby ensuring safety.

Also, because the power transmitting members is the third tube 41 having the third lumen 42 through which the guide wire 50 can be inserted, the catheter for removing foreign body in blood vessel 10 can be directed by the guide wire 50 to be reliably guided to a site, where the foreign substance is generated.

In addition, because the balloon 52 for guiding the foreign substance 2 into the capturing chamber 12A can be inserted through the third tube 41, the foreign substance 2 can be effectively guided and condensed into the capturing chamber 12A by the balloon 52. Meanwhile, the balloon 52 may be provided on the guide wire 50 as described above, and also, after other guide wires not having a balloon are used instead of the guide wire 50, a typical balloon catheter may be used.

Further, because as the radiographic makers, which allows a distance between the balloon 52 and the cutting unit 13 to be seen by eyes, the wire material 53 and the blades 44 are formed of materials having an X-ray contrast property, the balloon 52 and the blades 44 can be operated while checking locations thereof from the outside of the body, thereby preventing contact between the cutting unit 13 and the balloon 52 and thus avoiding damage of the balloon 52 by the cutting unit 13.

Further, because the cutting unit 13 is the plurality of foldable blades 44, even a large foreign substance 2 can be reliably sucked and removed by cutting and nodulizing the foreign substance 2 by the blades 44.

Further, because unevenness along a circumferential direction is formed on the inner surface of the capturing chamber 12A by the triangle column-shaped frame portions 31, the foreign substance 2 can be ground and crushed by the unevenness formed on the inner surface of the capturing chamber 12A and the blades 44, thereby effectively nodulizing the foreign substance 2.

In addition, because the third tube 41 can be moved relative to the second tube 23 only toward the distal end side thereof, the third tube 41 is moved relative to the second tube 23 toward the distal end side thereof after nodulizing the foreign substance 2, so that the nodulized foreign substance 2 can be effectively sucked from the proximal end opening 34 of the capturing chamber 12A. Also, during insertion into the blood vessel 1, movement of the third tube 41 relative to the second tube 23 toward the proximal end side thereof is restricted, so that when inserting the second tube 23 into the blood vessel 1, a location of the third tube 41 is restricted, thereby allowing an easy insertion of the second tube. Meanwhile, the third tube 41 may be configured to be movable relative to the second tube 23 toward the distal end side and the proximal end side.

Second Embodiment

Next, a second embodiment of a catheter for removing foreign body in blood vessel will be described with reference to FIGS. 5 and 6. Meanwhile, in an catheter for removing foreign body in blood vessel according to each of the following embodiments, a cutting unit is only different from that in the catheter for removing foreign body in blood vessel according to the first embodiment and the other portions are identical to those in the catheter for removing foreign body in blood vessel according to the first embodiment of the present invention, and accordingly, the cutting unit will be only illustrated and described.

Figure 5A:
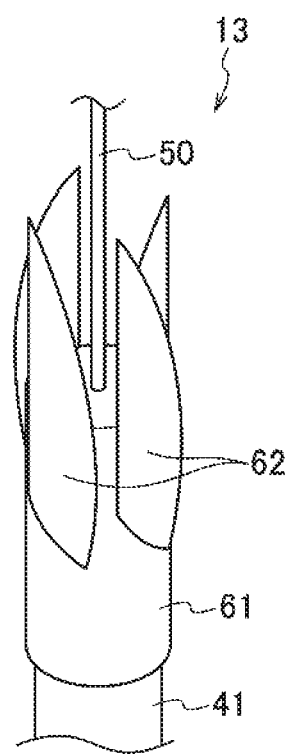
FIGS. 5A and 5B are perspective views of a cutting unit.
Figure 5B:
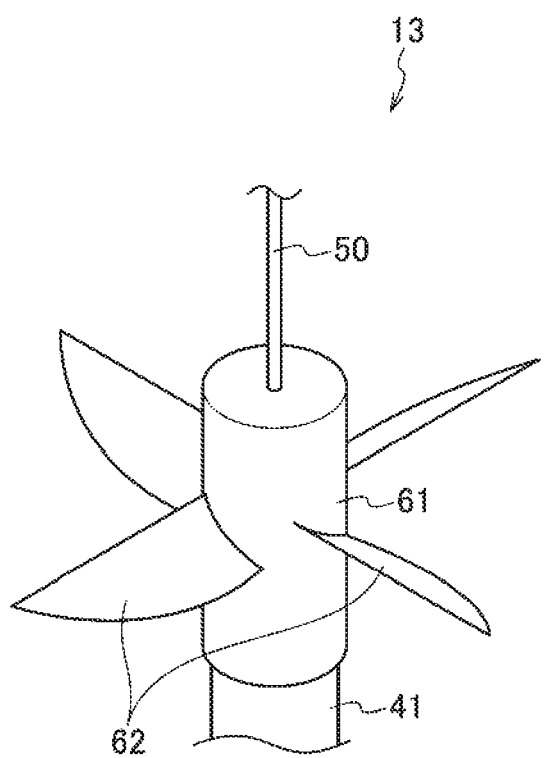
Figure 6:
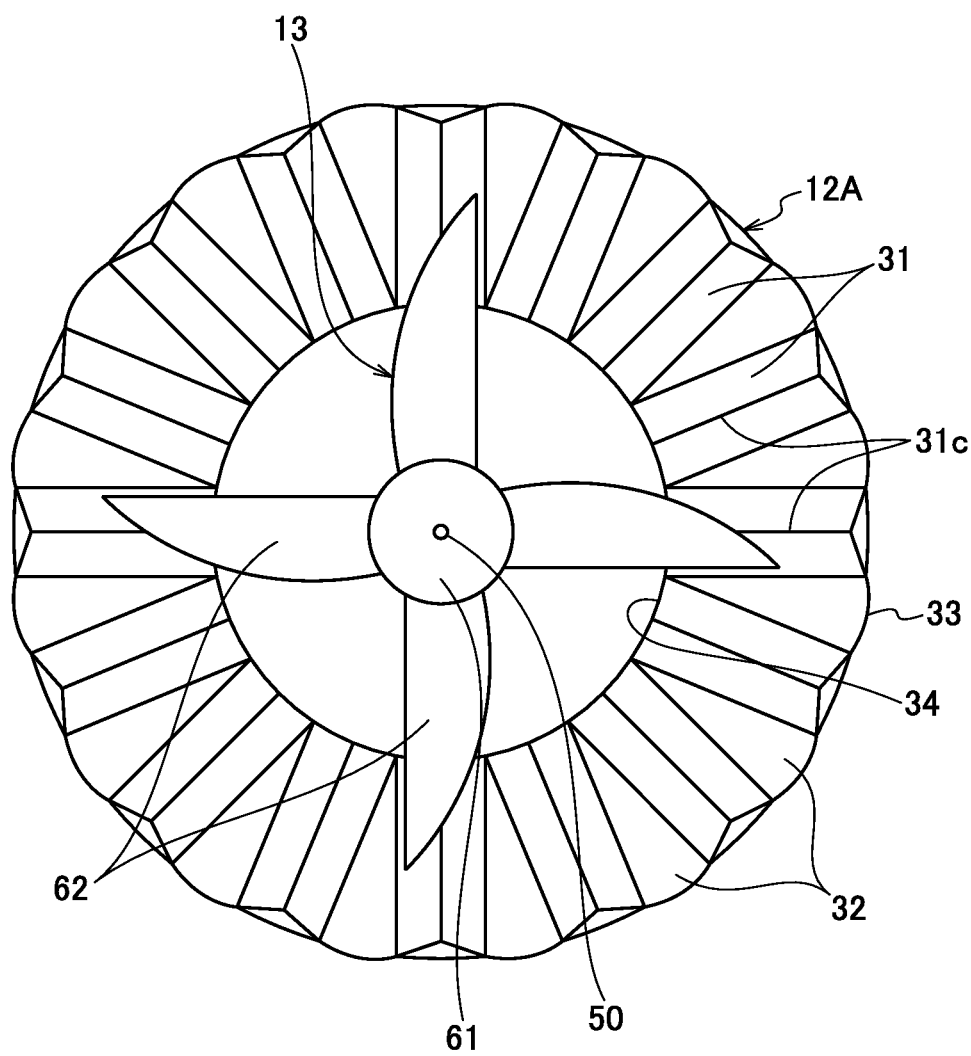
FIG. 6 is an enlarged top view of a capturing unit and the cutting unit, which are in an expanded state, according to the second embodiment.

FIG. 5A is a perspective view of a cutting unit, which is in a contracted state, according to the second embodiment, FIG. 5B is a perspective view of the cutting unit, which is in an expanded state, and FIG. 6 is an enlarged top view of a capturing unit and the cutting unit, which are in an expanded state, according to the second embodiment.

As shown in FIGS. 5 and 6, the cutting unit 13 of the catheter for removing foreign body in blood vessel 10 according to the second embodiment has a cylindrical base portion 61 fixed on a distal end of a third tube 41 and a plurality of propellers 62 (4 pieces in the embodiment shown in the drawings) provided on an outer peripheral surface of the cylindrical base portion 61 at equal intervals along a circumferential direction thereof.

The propellers 62 are formed of a shape memory alloy, in which an expanded state, where the propellers extend radially outward from the cylindrical base portion 61, is shape-memorized, and are deformable into a contracted state, in which, as shown in FIG. 5A, the propellers are constrained and received in a capturing unit 12 and folded along the outer peripheral surface of the cylindrical base portion 61, and an expanded state, in which, as shown in FIG. 5B, the propellers are radially deployed by a restoring force of the shape memory alloy. Meanwhile, the propellers 62 are preferably formed of an elastic material having an X-ray contrast property, so that a function of a radiographic marker can be imparted thereto.

As shown in FIG. 6, when the capturing unit 12, which has been pushed out from a distal end opening 22a of a first lumen 22, is expanded to form a capturing chamber 12A, the propellers 62, which have been received in the capturing unit 12 in the contracted state, are flared by the restoring force of the shape memory alloy to become the expanded state.

Then, by operating a spinning rod 43 to rotate the propellers 62, a foreign substance 2, such as thrombus, condensed in the capturing chamber 12A is cut and nodulized and then sucked and removed from a second port 26 to the outside of the body.

As described above, according to the catheter for removing foreign body in blood vessel 10 of the present embodiment, because the cutting unit 13 is the foldable propellers 62, even a large foreign substance 2 can be reliably sucked and removed by reliably cutting and nodulizing the foreign substance 2 by the propellers 62.

Third Embodiment

Next, a third embodiment of a catheter for removing foreign body in blood vessel according to the present invention will be described with reference to FIGS. 7 and 8.

Figure 8:
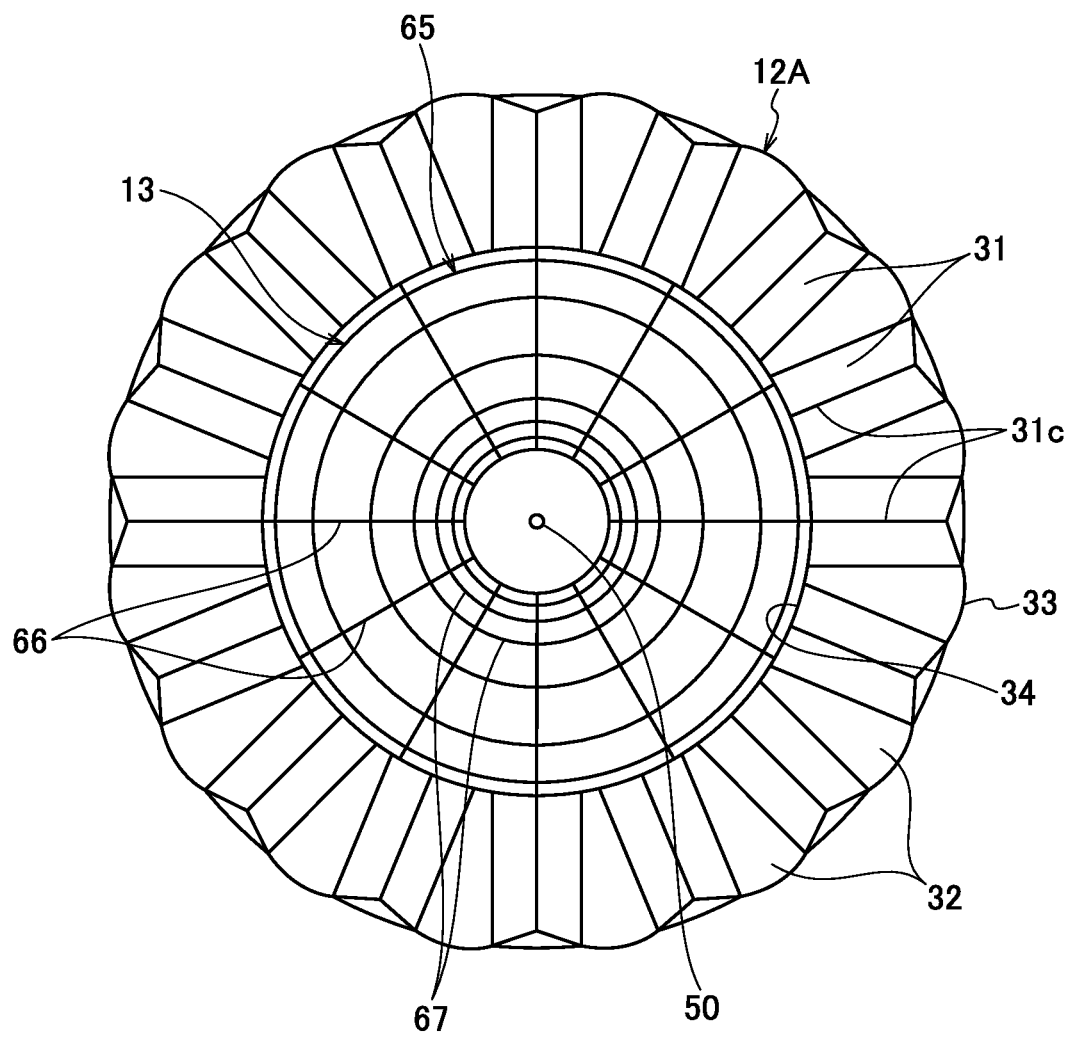
FIG. 8 is an enlarged top view of a capturing unit and the cutting unit, which are in an expanded state, according to the third embodiment.

As shown in FIGS. 7 and 8, the cutting unit 13 of the present embodiment is formed of a meshed member 65. The meshed member 65 is constituted of a plurality of wire materials 66 fixed on a distal end of a third tube 41 and extending in an axial direction and ring-shaped wire materials 67 coupled to the plurality of wire materials 66 at predetermined intervals. Meanwhile, lengths of the ring-shaped wire materials 67 are set to have the shortest length in ring-shaped wire materials 67 arranged on end sides of the wire materials 66 and to be gradually lengthened as they go toward the middle part in an axial direction of the wire materials 66.

The wire materials 66 are formed of a shape memory alloy, which is shape-memorized to have a generally elliptical shape in a natural state, and are deformable into an contracted state, in which, as shown in FIG. 7A, the wire materials 66 become a linear state to form a meshed cylinder, and an expanded state, in which, as shown in FIG. 7B, due to a restoring force of the shape-memorized wire materials 66, the middle part in the axial direction thereof is swelled radially outward. Meanwhile, the meshed member 65 is preferably formed of an elastic material having an X-ray contrast property, so that a function of a radiographic marker can be imparted thereto.

When a capturing unit 12 is pushed out from a distal end opening 22a of the first lumen 22, the plurality of wire materials 66 constituting the meshed member 65 are released from constraint by the first lumen 22, and thus the middle part thereof is swelled radially outward by the self-restoring thereof to be deformed into a generally elliptical shape, thereby forming a capturing chamber 12A.

Then, by operating a spinning rod 43 to rotate the meshed member 65, a foreign substance 2, such as thrombus, condensed in the capturing chamber 12A is cut and nodulized by the meshed member 65 and then sucked and removed from a second port 26 to the outside of the body.

As described above, according to the catheter for removing foreign body in blood vessel 10 of the present embodiment, because the cutting unit 13 is the expandable meshed member 65, even a large foreign substance 2 can be reliably sucked and removed by reliably cutting and nodulizing the foreign substance 2 by the meshed member 65.

Meanwhile, the present invention is not limited to each of the foregoing embodiments, and accordingly, appropriate changes, modifications or the like thereof can be made.

For examples, a vibration generating member may be provided on the capturing unit 12, the cutting unit 13, the balloon 52 and the like, so that the vibration generating member can generate a vibration by operation of a user. In this case, due to the vibration of the vibration generating member, a vibration can be applied to the foreign substance flowed into the capturing chamber 12A, so that the foreign substance becomes smaller pieces to easily flow.

In addition, the sheath 11 is not necessary to include the first tube 21 having the first lumen 22 and the second tube 23 having the second lumen 24, but may be constituted of only the second tube 23 having the second lumen 24, and thus, a member corresponding to the first tube 21 having the first lumen 22 may be separately prepared during surgery and also may be employed as a guiding catheter used in other treatments. Therefore, for example, when a stent or the like is indwelled after removing a foreign substance, an operation can be performed with the guiding catheter remained.

More specifically, if the guiding catheter is used instead of the first tube 21 of the sheath 11, when the sheath 11 is withdrawn, the second and third tubes 23 and 41 are withdrawn with the guiding catheter remained as it is. In this state, an indwelling catheter for indwelling a stent or the like is inserted into a blood vessel and reaches an indwelling site through the inside of the guiding catheter, and then the stent or the like is indwelled.

REFERENCE NUMERALS LIST

2 Foreign substance
10 Catheter for removing foreign body in blood vessel

11 Sheath
12 Capturing unit
12A Capturing chamber
13 Cutting unit
21 First tube
22 First lumen
22a Opening
23 Second tube (Tube)
24 Second lumen
33 Distal end opening
34 Proximal end opening
41 Third tube (Power transmitting member)
42 Third lumen
44 Blade (Cutting unit, Propeller-shaped member)
50 Guide wire
53 Balloon (Guide unit)
53 Wire material (Protection member)
62 Propeller (Cutting unit, Propeller-shaped member)
65 Meshed member (Cutting unit)

The invention claimed is:

1. A catheter for removing a foreign substance in a blood vessel, the catheter comprising:
a tube configured to be inserted in the blood vessel; and
a capturing unit provided on a distal end of the tube and configured to be radially expandable and to be guided into the blood vessel through the tube to capture the foreign substance in the blood vessel; and
a guide unit configured to guide a foreign substance between the guide unit and the capturing unit toward the capturing unit, the guide unit comprising wire members, each of the wire members being convex toward a wall of the blood vessel when the guide unit is placed inside the blood vessel,
wherein the capturing unit includes a plurality of frame portions and a plurality of sheet portions,
wherein the capturing unit forms a capturing chamber, an opening area of which is decreased as it goes from a distal end opening of the capturing chamber toward a proximal end opening of the capturing chamber in an expanded state of the capturing chamber,
wherein each of the plurality of frame portions has a same shape, and the plurality of frame portions are arranged circumferentially at a constant regularity,
wherein each of the plurality of frame portions includes a protrusion provided only on an inner side of the capturing unit,
wherein the plurality of frame portions and the plurality of sheet portions are alternatively arranged around an axis centered on a tube axis of the catheter,
wherein, in a contracted state, the capturing unit is configured so that a distal end sides of the plurality of frame portions are gathered in a circumference shape and the sheet portions are folded on only an outer side of the capturing unit,
wherein each of the plurality of protrusions extends in the axial direction from a proximal end to a distal end of the capturing unit, and
wherein, in the expanded state, each of the plurality of sheet portions cover between adjacent frame portions of the plurality of frame portions in a membrane shape.

2. The catheter according to claim 1, wherein the capturing unit is configured such that an outer side of the capturing unit touches the wall of the blood vessel when the capturing unit is expanded.

3. The catheter according to claim 1, wherein the capturing unit and the guide unit are sized such that the foreign substance guided toward the capturing unit is nodulized between the plurality of frame portions of the capturing unit and the wire members of the guide unit.

4. The catheter according to claim 1, wherein the capturing unit comprises a portion configured to expand in a bowl shape extending from an end of the tube when the capturing unit is in the expanded state.

5. The catheter according to claim 1, wherein the plurality of sheet portions are configured to cover gaps between the plurality of frame portions.

6. The catheter according to claim 1, wherein each of the plurality of frame members is column shaped.

7. The catheter according to claim 6, wherein each of the plurality of frame members is a triangular column shape.

8. The catheter according to claim 1, wherein the guide unit comprises a balloon.

* * * * *